US00PP17343P2

(12) United States Plant Patent
Holtmaat

(10) Patent No.: US PP17,343 P2
(45) Date of Patent: Jan. 9, 2007

(54) ***ASTILBE* PLANT NAMED 'BEAUTY OF ERNST'**

(50) Latin Name: *Astilbe hybrida*
Varietal Denomination: Beauty of Ernst

(75) Inventor: Henk Holtmaat, Zuidwolde (NL)

(73) Assignee: Jac. Th. de Vrooman, Lisse (NL)

( * ) Notice: Subject to any disclaimer, the term of this patent is extended or adjusted under 35 U.S.C. 154(b) by 53 days.

(21) Appl. No.: 11/097,674

(22) Filed: Mar. 31, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Astilbe* plant named 'Beauty of Ernst', characterized by its upright plant habit; rapid growth rate; brightly colored foliage; freely and uniform flowering habit; and light pink-colored flowers arranged on upright to slightly arching inflorescences.

2 Drawing Sheets

Botanical designation: *Astilbe hybrida.*
Cultivar denomination: 'Beauty of Ernst'.

BACKGROUND OF THE INVENTION

The present Invention relates to a new and distinct cultivar of *Astilbe* plant, botanically known as *Astilbe hybrida*, and hereinafter referred to by the name 'Beauty of Ernst'.

The new *Astilbe* is a product of a planned breeding program conducted by the Inventor in Zuidwolde, The Netherlands. The objective of the breeding program was to develop new fast-growing *Astilbe* cultivars with attractive foliage coloration.

The new *Astilbe* originated from a chance pollination of two unknown *Astilbe hybrida* selections. The new *Astilbe* was discovered and selected as a single flowering plant by the Inventor in a controlled environment in Zuidwolde, The Netherlands on the basis of its unique foliage coloration.

Asexual reproduction of the new cultivar by root divisions in Zuidwolde, The Netherlands, has shown that the unique features of this new *Astilbe* are stable and reproduced true to type in successive generations.

SUMMARY OF THE INVENTION

Plants of the cultivar Beauty of Ernst have not been observed under all possible environmental conditions. The phenotype may vary somewhat with variations in environment such as temperature and light intensity without, however, any variance in genotype.

The following traits have been repeatedly observed and are determined to be the unique characteristics of 'Beauty of Ernst'. These characteristics in combination distinguish 'Beauty of Ernst' as a new and distinct *Astilbe* cultivar:

1. Upright plant habit.
2. Rapid growth rate.
3. Brightly colored foliage.
4. Freely and uniform flowering habit.
5. Light pink-colored flowers arranged on upright to slightly arching inflorescences.

Plants of the new *Astilbe* can be compared to the *Astilbe* cultivar Brautschleier, not patented. In side-by-side comparisons conducted in Zuidwolde, The Netherlands, plants of the new *Astilbe* differed from plants of the cultivar Brautschleier primarily in flower coloration.

Plants of the new *Astilbe* can also be compared to the *Astilbe* cultivar Anita Pfeifer, not patented. In side-by-side comparisons conducted in Zuidwolde, The Netherlands, plants of the new *Astilbe* differed from plants of the cultivar Anita Pfeifer in the following characteristics:

1. Plants of the new *Astilbe* and the cultivar Anita Pfeifer differed in leaf shape.
2. Plants of the new *Astilbe* and the cultivar Anita Pfeifer differed in foliage coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Astilbe.*

The photograph on the first sheet comprises a side perspective view of a typical flowering plant of 'Beauty of Ernst' grown in a container.

The photograph at the top of the second sheet is a close-up view of a typical inflorescence of 'Beauty of Ernst'.

The photograph at the bottom of the second sheet is a close-up view of the foliage of 'Beauty of Ernst'.

DETAILED BOTANICAL DESCRIPTION

Plants shown in the aforementioned photographs and used in the following description were grown in 17-cm containers under conditions which closely approximate commercial production conditions during the spring and summer in an outdoor nursery in Zuidwolde, The Netherlands. Plants were about one year old when the photographs and description were taken. During the production of the plants, day temperatures ranged from 5 to 20° C. and night temperatures ranged from 2 to 12° C. In the following description, color references are made to The Royal Horticultural Society Colour Chart, 1995 Edition, except where general terms of ordinary dictionary significance are used.

Botanical classification: *Astilbe hybrida* cultivar Beauty of Ernst.

Parentage:

*Female, or seed, parent.*—Unknown selection of *Astilbe hybrida.*

*Male, or pollen, parent.*—Unknown selection of *Astilbe hybrida.*

Propagation:

*Type.*—By root divisions.

*Time to initiate rooting, summer.*—About 30 days at 18° C.

*Time to initiate rooting, winter.*—About 40 days at 18° C.

*Time to produce a rooted young plant.*—About 25 weeks at 18°.

*Root description.*—Fine.

Plant description:

*Form.*—Perennial. Upright plant habit; inverted triangle. Flowering stems and leaves arise from the roots; dense and bushy plant habit; moderately vigorous growth habit. Freely flowering with numerous flowers on numerous branched panicles.

*Growth rate.*—Rapid; from divisions, about 20 weeks are required to produce fully-grown flowering plants in 17-cm containers.

*Plant height.*—About 75 cm.

*Plant width.*—About 50 cm.

*Stem description.*—Length: About 75 cm. Diameter: About 5 mm. Internode length: About 10 cm. Strength: Strong. Texture: Sparsely pubescent. Color: Close to 139A.

*Foliage description.*—Arrangement: Alternate; bi-ternately compound. Leaf length (including petiole): About 35 cm. Leaf width: About 20 cm. Leaflet length: About 8 cm. Leaflet width: About 3.6 cm. Leaflet shape: Ovate to elliptic. Leaflet apex: Acuminate to acute. Leaflet base: Cuneate to oblique. Leaflet margin: Serrate or occasionally biserrate. Leaflet texture, upper and lower surfaces: Sparsely pubescent. Leaflet luster, upper and lower surfaces: Slightly lustrous. Leaflet venation pattern: Pinnate. Leaflet color: Developing and fully expanded foliage, upper surface: 137D, 165A, 180B or 183A; venation, 141A or 183A. Developing and fully expanded foliage, lower surface: 138A or 178A; venation, 180B to 181A. Petiole length: About 15 cm. Petiole diameter: About 2.5 mm. Petiole texture, upper and lower surfaces: Smooth, glabrous. Petiole color, upper surface: 46A. Petiole color, lower surface: 179C.

Flower description:

*Flower arrangement and shape.*—Small single flowers arranged in upright to slightly arching branched panicles; flowers face upright, outward or droop. Freely and uniformly flowering habit; about 1,000 flowers and flower buds per plant.

*Natural flowering season.*—Continuous flowering during the early summer in The Netherlands.

*Flower longevity on the plant.*—Individual flowers last several weeks on the plant and about one week as a cut flower. Flowers persistent.

*Fragrance.*—Faint; musty, but not unpleasant.

*Flower buds.*—Length: About 1.5 mm. Diameter: About 1.5 mm. Shape: Ovate to orbicular. Color: 164D.

*Flowers.*—Diameter: About 7 mm. Depth (height): About 2 mm.

*Petals.*—Quantity per flower: About five. Length: About 3.5 mm. Width: About 2 mm. Shape: Ligulate to linear. Apex: Obtuse. Margin: Entire. Texture, upper and lower surfaces: Smooth, glabrous. Color: When opening, upper and lower surfaces: 55D. Fully opened, upper and lower surfaces: 56D.

*Sepals.*—Quantity per flower: About five. Length: About 5 mm. Width: About 6 mm. Shape: Ovate. Apex: Obtuse. Base: Cuneate, fused. Margin: Entire. Texture, upper and lower surfaces: Smooth, glabrous. Color: Immature, upper and lower surfaces: 164D. Mature, upper and lower surfaces: 164D.

*Reproductive organs.*—Stamens: Quantity per flower: About ten. Anther attachment: Basifixed. Anther shape: Oblong. Anther length: Less than 0.5 mm. Anther color: Close to 158A. Pollen amount: Scarce. Pollen color: 19A. Pistils: Quantity per flower: Two. Pistil length: About 2 mm. Stigma shape: Club-shaped. Stigma color: Close to 86B. Style length: About 1.5 mm. Style color: Close to 87D. Ovary color: Close to 87D.

*Seeds.*—Length: Less than 0.5 mm. Diameter: Less than 0.5 mm. Color: Light brown.

Disease/pest resistance: Plants of the new *Astilbe* have not been noted to be resistant to pathogens and pests common to *Astilbe.*

High temperature tolerance: Plants of the new *Astilbe* have been observed to tolerate temperatures of 30° C.

Hardiness: Plants of the new *Astilbe* are hardy to USDA Zone 5.

It is claimed:

1. A new and distinct cultivar of *Astilbe* plant named 'Beauty of Ernst', as illustrated and described.

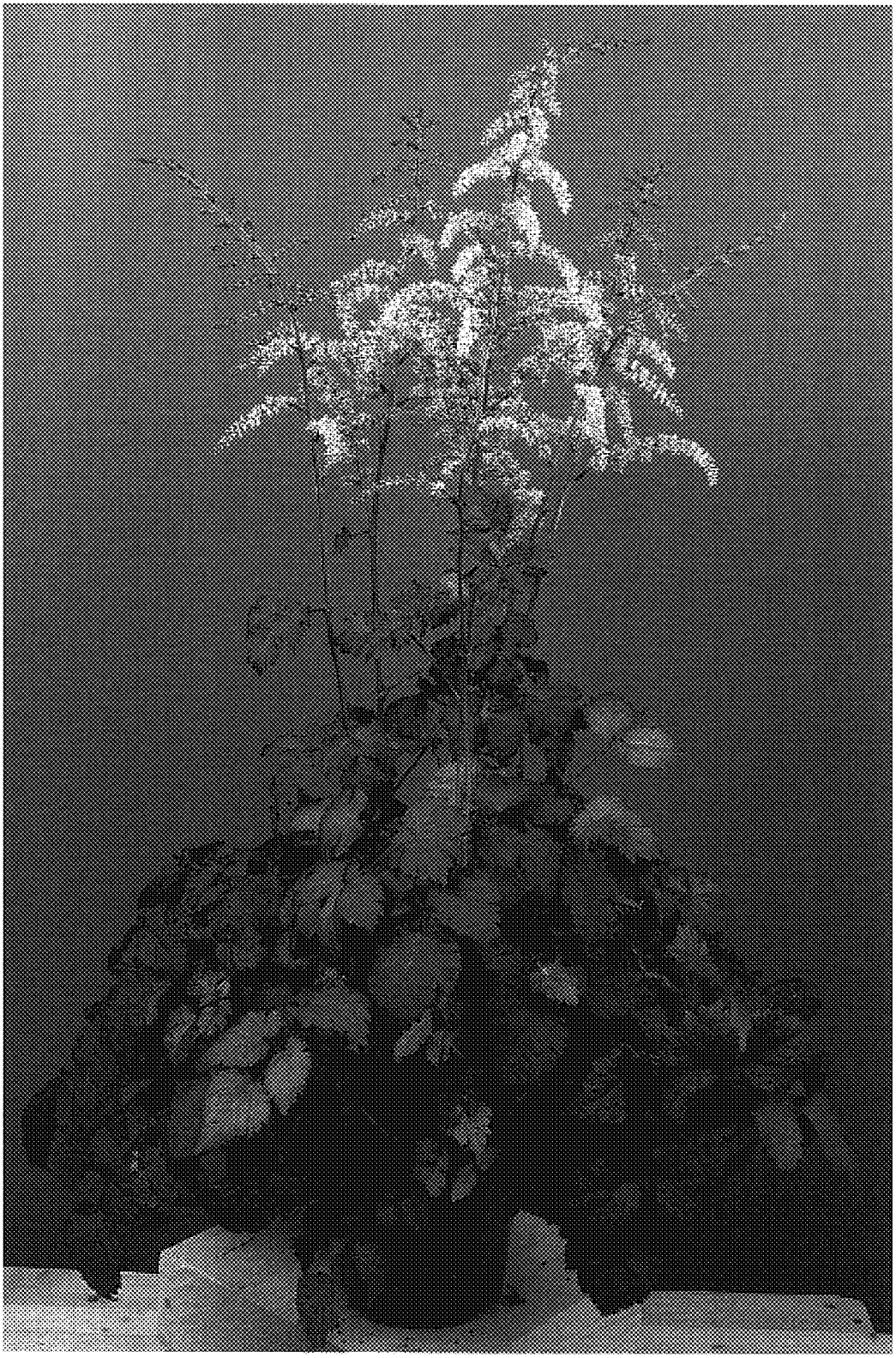

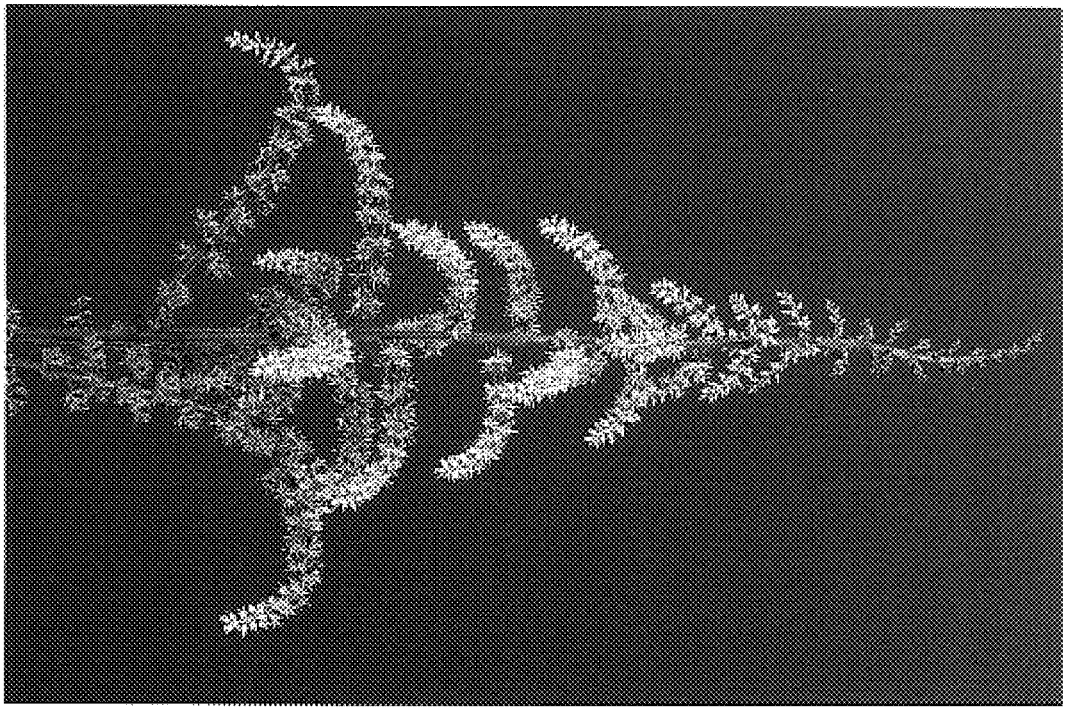
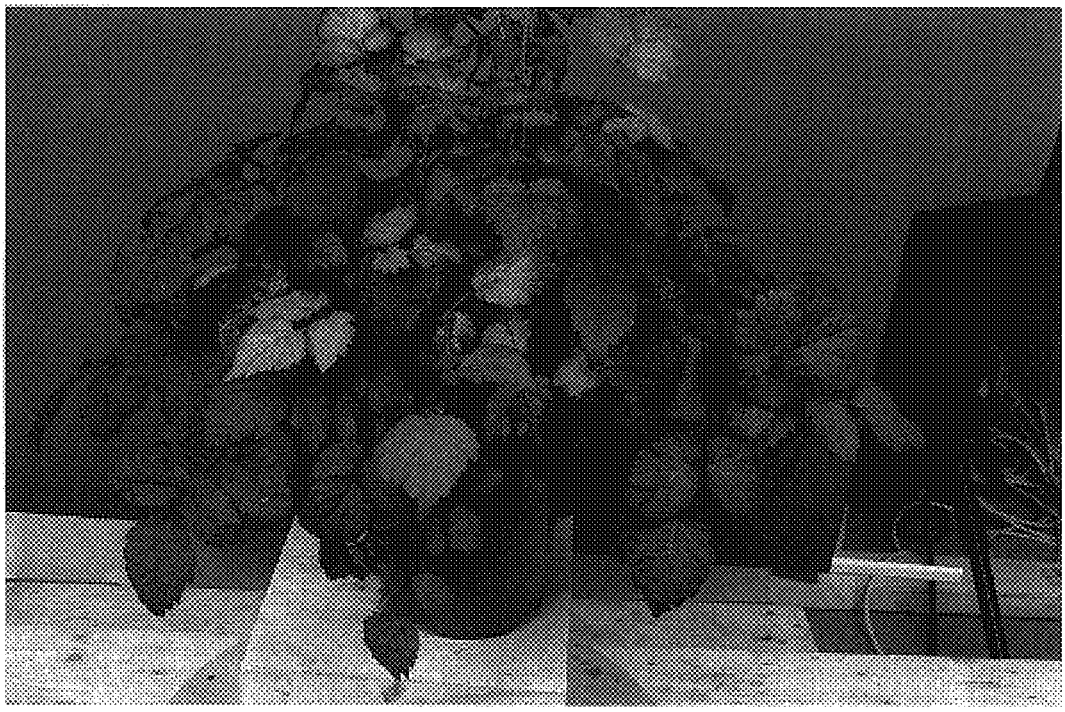

* * * * *